United States Patent [19]

Fruehwirth

[11] Patent Number: Plant 7,235

[45] Date of Patent: May 22, 1990

[54] POINSETTIA PLANT 'C-27'

[75] Inventor: Franz Fruehwirth, Encinitas, Calif.

[73] Assignee: Paul Ecke Ranch, Inc., Encinitas, Calif.

[21] Appl. No.: 263,496

[22] Filed: Oct. 27, 1988

[51] Int. Cl.[5] ..... A01H 5/00

[52] U.S. Cl. ..... Plt./86

[58] Field of Search ..... Plt./86

[56] References Cited

U.S. PATENT DOCUMENTS 4,724,276 2/1988 Ecke ..... 800/1

*Primary Examiner*—James R. Feyrer

*Attorney, Agent, or Firm*—Arnold, White & Durkee

[57] ABSTRACT

A new Poinsettia cultivar, 'C-27', is described, particularly distinguished by its large, bright red, erect flower bracts. This new Poinsettia cultivar, has extra perky bright red bracts which do not droop and even tend to bend upwards. This Poinsettia grows very fast as a single stemmed plant, upright and vigorous. Typical leaves are ovate with obtuse bases and acuminate tips. The color of the upper side of the bracts is bright red, between RHS 45A and 45B, and under side near RHS 47A.

1 Drawing Sheet

BACKGROUND OF THE INVENTION

The Poinsettia of the present invention, cultivar 'C-27', is a stiff-stemmed, vigorous Poinsettia with large, bright red, erect flower bracts. It is unique because the flower bracts remain erect and do not droop even after commercial shipping and handling or as the flowers mature. It always looks "fresh" which adds to its beauty and increases its value as a consumer product. The cultivar 'C-27' can be grown in a relatively cool greenhouse, making it more economical to grow commercially.

This new Poinsettia cultivar originated as a seedling from cross pollination of Poinsettias in a greenhouse in Encinitas, Calif. It was selected from many seedlings because of traits which distinguish it from other oinsettia cultivars, and seem to make it a desirable plant for commercial greenhouse production. After selection, this plant was vegetatively reproduced by stem cuttings for test purposed in Encinitas, Calif., and clones of this plant were subjected to successive generations of vegetative propagation which demonstrated that its distinctive characteristics hold true from generation to generation.

DESCRIPTION OF THE PHOTOGRAPHS

'C-27' is illustrated in the accompanying color photographs. The upper photo is a side view of a typical pot plant in full flower. The lower photo is a top view of the same plant showing flower bract formation.

DESCRIPTION OF THE PLANT

The following is a detailed description of this new Poinsettia as observed during December, 1987. Recorded observations from flowering plants, grown as 3 unpinched plants per pot. The pot was 14 cm. in diameter and 11 cm. in height. Color designations were compared to the 1986 edition of R.H.S. Colour Chart, first published in 1966 by The Royal Horticultural Society, London England.

THE PLANT

Origin: Seedling.

Classification:

*Botanic.*—*Euphorbia pulcherrima* Willd.

*Common name.*—Poinsettia.

*Cultivar name.*—'C-27'.

Form: Shrub.

Height: Medium.

Growth habit: As a single stemmed plant, upright and vigorous. The application of a chemical growth retardant may be needed to restrict height for commercial pot plant production. Three plants in a pot with an overall height of 43 cm. and an overall width of 48 cm. was observed. The bract diameter of individual flowers was 32–34 cm.

Branching: Branching can be induced by removal of the step tip. Then, 3–5 flowering branches may develop on a single plant. Under normal culture practices, this plant does not generally develope axillary branches, without removing the terminal dominance by pinching. It is not a self-branching cultivar. Commercially, it is valuable for those who wish to market single-stemmed plants with large, showy bracts. If pinched, one could expect 3–5 axially branches to develop uniformly.

Cyathia: Generally, 15–18 cyathia (flowers) are present when the plant is in "full bloom". Each cyathium is about 8 mm long and about 5 mm wide, light green in color, and fringed with red at the distal end. Usually one bright yellow nectar cup protrudes from the side of the cyathium. The flower pedicel is also light green and about 5–6 mm in length. The anthers protruding from the cyathia are red.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being about 12–14 cm. long and about 11–12 cm. wide with leaf petioles about 4–6 cm. long.

Leaf shape: Typical leaves are ovate with obtuse bases and acuminate tips. Leaf margins are usually lobed with 2 indentations on each side of the leaf blade.

Color:

*Upper side.*—Darker than RHS 147A.

Retention: The foliage lasts extremely well even under low light intensities in the consumer's home.

Bracts: Generally there are 21–24 uniformly colored bracts of various sizes subtending the cyathia. The primary bracts have blades typically 15–17 cm. long and 10–11 cm. wide with petioles about 3 cm. long.

Shape: Bracts are mostly ovate with acute bases and acuminate tips. Primary bracts are lobed with two indentations on either side of the Bract.

Color:

Upper side.—Bright red, between RHS 45A and RHS 45B.

*Under side.*—Near RHS 47A.

What is claimed:

1. A new and distinct Poinsettia cultivar, substantially as herein shown and described, distinguished by its large, bright red, erect flower bracts which tend to bend upwards.

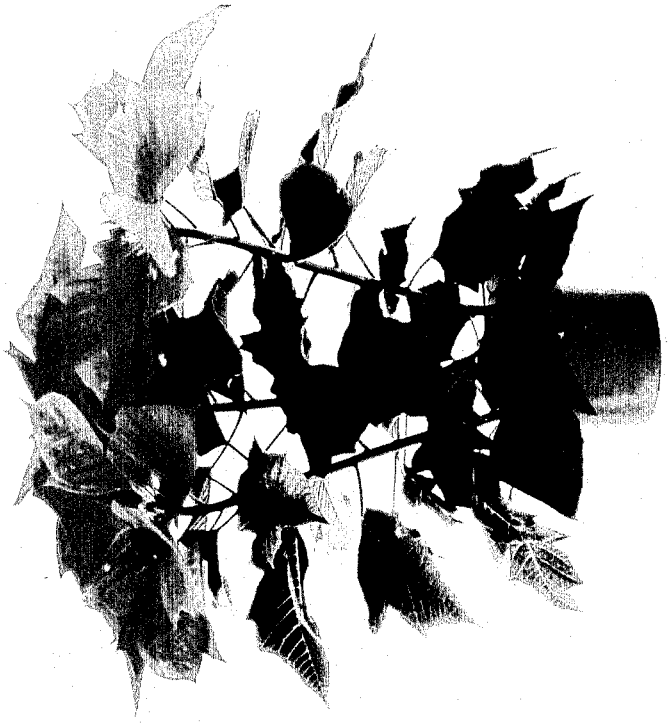
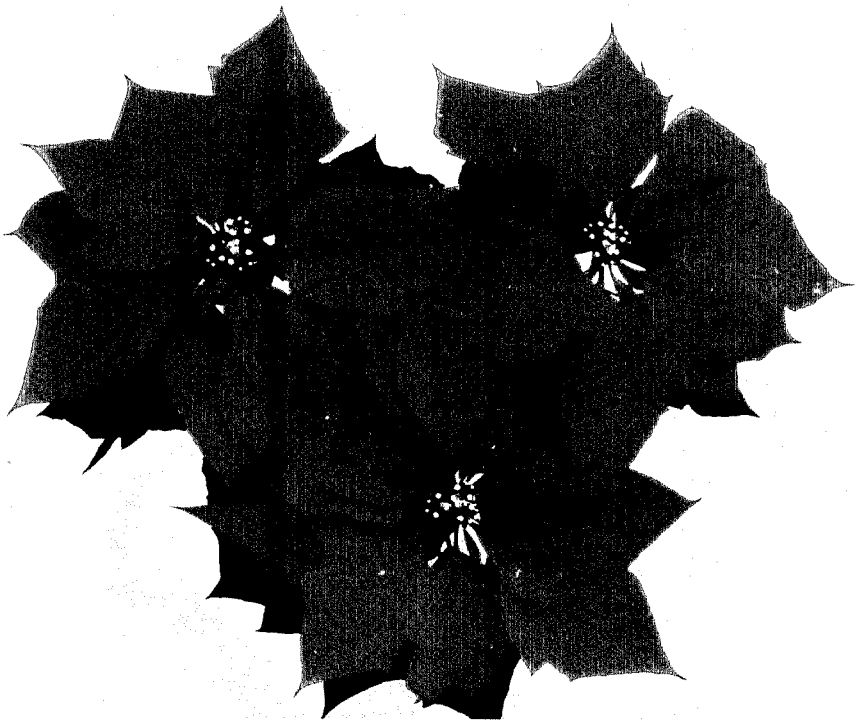

* * * * *